United States Patent [19]

Levin

[11] Patent Number: 5,100,626
[45] Date of Patent: Mar. 31, 1992

[54] BINDING ASSAY DEVICE WITH REMOVABLE CASSETTE AND MANIFOLD

[76] Inventor: Andrew E. Levin, 10 Gay Rd., Watertown, Mass. 02172

[21] Appl. No.: 528,824

[22] Filed: May 24, 1990

[51] Int. Cl.$^5$ ............................................. G01N 33/48
[52] U.S. Cl. .................................. 422/100; 422/101; 422/103; 435/293; 435/301
[58] Field of Search ............................... 422/100–104; 435/293, 301

[56] References Cited

U.S. PATENT DOCUMENTS

| | | |
|---|---|---|
| 3,378,347 | 4/1968 | Saravis . |
| 4,031,197 | 6/1977 | Marinkovich . |
| 4,452,901 | 6/1984 | Gordon et al. .................... 436/506 |
| 4,585,623 | 4/1986 | Chandler ....................... 422/100 X |
| 4,665,034 | 5/1987 | Chandler ....................... 422/100 X |
| 4,713,349 | 12/1987 | Levin ............................... 436/515 |
| 4,725,406 | 2/1988 | Compton et al. ................. 422/104 |
| 4,834,946 | 5/1989 | Levin ............................... 422/101 |
| 4,859,419 | 8/1989 | Marks et al. ................. 422/103 X |
| 4,868,123 | 9/1989 | Berson et al. ................. 435/301 X |
| 4,978,507 | 12/1990 | Levin ............................... 422/100 |
| 5,011,779 | 4/1991 | Maimon ....................... 422/104 X |
| 5,043,581 | 8/1991 | Joss ............................. 422/102 X |
| 5,047,215 | 9/1991 | Manns ............................. 422/101 |

FOREIGN PATENT DOCUMENTS 2099578 4/1982 United Kingdom .

OTHER PUBLICATIONS 1988 brochure on a "Miniblotter System" for multiple antibody screening on Western Blots, Immunetics.
1989 Innogenetics brochure advertising assay strips for detection of multiple antigens.

*Primary Examiner*—Robert J. Hill, Jr.
*Attorney, Agent, or Firm*—Harness, Dickey & Pierce

[57] ABSTRACT

The binding assay device of the present invention provides a removable cassette with an array of parallel channels for receiving multiple samples for assay. The cassette generally comprises a substantially planar cassette base with open channels formed in its bottom surface and a pair of channel extensions extending from its top surface which contain closed channels corresponding to and in fluid communication with open channels. The closed channels are further provided with openings at their termini for introduction of test samples into the cassette. In an assembled device, the cassette is disposed between a base plate and a slotted cover plate adapted for receipt of the channel extensions of the cassette. A resilient cushioning pad placed between the cassette base and base plate improves interchannel sealing and reduces the volume of the base channels and samples needed. A removable manifold adapted for sealing engagement with a channel extension and in fluid communication with the channels of the cassette facilitates simultaneous flushing of the channels.

In assaying for a analyte, a membrane on which binding member specific for the analyte is immobilized is placed between the resilient pad and the open channelled bottom surface of the cassette base. After the plates have been fastened together to secure the membrane in place under the cassette, the channels of the cassette are filled with appropriate volumes of test samples and assay reagents under conditions allowing binding and/or signaling events to occur. The channels are then flushed to rinse away unbound materials. Additional reagents, indicators, or binding members can also be introduced into the channels to provide a detectable signal.

37 Claims, 8 Drawing Sheets

BINDING ASSAY DEVICE WITH REMOVABLE CASSETTE AND MANIFOLD

FIELD OF THE INVENTION

The present invention relates generally to an improved binding assay device and, more particularly, to a binding assay device having a removable cassette for the receipt of test samples and an improved manifold for flushing the device. The device of the invention and improvements thereon relate generally to the types of devices disclosed in my prior application Ser. No. 200,135 filed May 31, 1988 entitled "Fluid Flow Manifold For Blot Type Screening Apparatus", now U.S. Pat. No. 4,978,507, and in my prior U.S. Pat. No. 4,834,946 issued May 30, 1989, entitled "Apparatus For Blot Screening Numerous, Small Volume, Antibody Solutions" and U.S. Pat. No. 4,713,349 issued Dec. 15, 1987, entitled "Templet For Simultaneous Screening Of Several Antibodies And Method Of Using The Same" and its continuation Ser. No. 131,960 filed Dec. 11, 1989 of the same title.

BACKGROUND OF THE INVENTION

Binding assays are routinely used to screen for and diagnose a whole host of diseases and conditions, including Lyme disease, herpes, acquired immunodeficiency syndrome, streptococcal infections, lupus and pregnancy, to name just a few. Such assays are relatively simple in theory, utilizing the binding affinity between two or more binding members to detect and/or quantify the presence of one of the members, referred to herein as the analyte. Binding members comprise a wide range of substances, including antigens, antibodies haptens, complimentarynucleic acid sequences, ligands and receptors, with antigen-antibody binding member pairs used in immunoassays currently enjoying the most widespread use.

One common format of a binding assay involves immobilizing a binding member specific for the analyte on a paperlike sheet or membrane. The membrane is then contacted with the test sample and appropriate reagents under conditions allowing binding to occur between the immobilized binding member and any analyte present in the sample, with means for detecting binding events also provided. Often a labelled second binding member which binds to the first binding member-analyte complex is added to provide a detectable signal on the membrane.

In the assay format described above, i.e. where the vehicle for the assay is a binding member immobilized on a membrane, a variety of devices and techniques have been developed for testing more than a single sample per membrane. For example, as described in my U.S. Pat. No. 4,834,946 and U.S. Pat. No. 4,713,349, a membrane is secured between two plates and samples applied in multiple plate channels. The devices and techniques currently available, however, require a significant degree of handling of the samples and membrane, increasing the possibility of contamination and widening the margin for human error. Thus there remains a need for an improved binding assay device for the accurate and efficient assaying of multiple samples which is convenient, easy to use, and which requires minimal handling of the assay components. Such an assay device is provided in accordance with the principles of the present invention.

SUMMARY OF THE INVENTION

The binding assay device of the present invention comprises a removable cassette containing an array of parallel channnesl for receiving multiple samples for assay. The cassette of the invention generally comprises a substantially planar cassette base with open channels formed in its bottom surface. A pair of channel extensions extending from the top surface of the cassette base contain closed channels corresponding to and in fluid communication with the open channels of the base. Test samples are introduced into the cassette channels through channel openings at the termini of the closed channels. In an assembled device, the cassette is disposed between a substantially planar base plate and a slotted cover plate which receives the channel extensions of the cassette. A resilient cushioning pad placed between the cassette base and base plate improves interchannel sealing and reduces the volume of the base channels and sample solutions needed.

In assaying for an analyte in accordance with the principles of the present invention, a membrane on which a binding member specific for the analyte is immobilized is placed between the resilient pad and the open channelled bottom surface of the cassette base. A gas-impermeable film can be provided between the membrane and pad or laminated onto the pad to prevent gas diffusion into the channels during the assay process. After the plates have been fastened together to secure the membrane in place under the cassette, the channels of the cassette are filled with appropriate volumes of test samples and assay reagents under conditions allowing binding and/or signaling events to occur on the membrane. The channels are then flushed to rinse away unbound materials. Additional reagents, indicators, or binding members can also be introduced into the channels to provide a detectable signal.

A removable manifold for simultaneous rinsing or washing of the array of channels is also provided. The manifold of the invention generally comprises a base portion and a leg portion extending therefrom. The base portion includes an opening through which fluids are introduced into or removed from the manifold. The leg portion contains an elongated groove in fluid communication with the manifold opening. When the manifold is in use, the leg portion is inserted over a channel extension of the cassette, placing the leg groove in fluid communication with the channel openings and channels of the cassette. Thus assay and wash solutions can be simultaneously introduced into or removed from all channels of the cassette.

The cassette of the invention can be preassembled and packaged with the membrane and pad as a hermetically-sealed unit and provided to the consumer for single and disposable use. The membrane provided can also include several different binding members immobilized thereon to permit simultaneous screening for the presence of more than one analyte.

Additional advantages and features of the present invention will become apparent from the following description and appended claims, taken in conjunction with the accompanying drawings.

BRIEF DESCRIPTION OF THE DRAWINGS

FIG. 4b is an enlarged view of a portion of the cassette of FIG. 4a.

FIG. 14 is a cross-sectional view of a second preferred embodiment of a manifold cartridge of the present invention.

DETAILED DESCRIPTION OF THE PREFERRED EMBODIMENTS OF THE INVENTION

Figure 1:
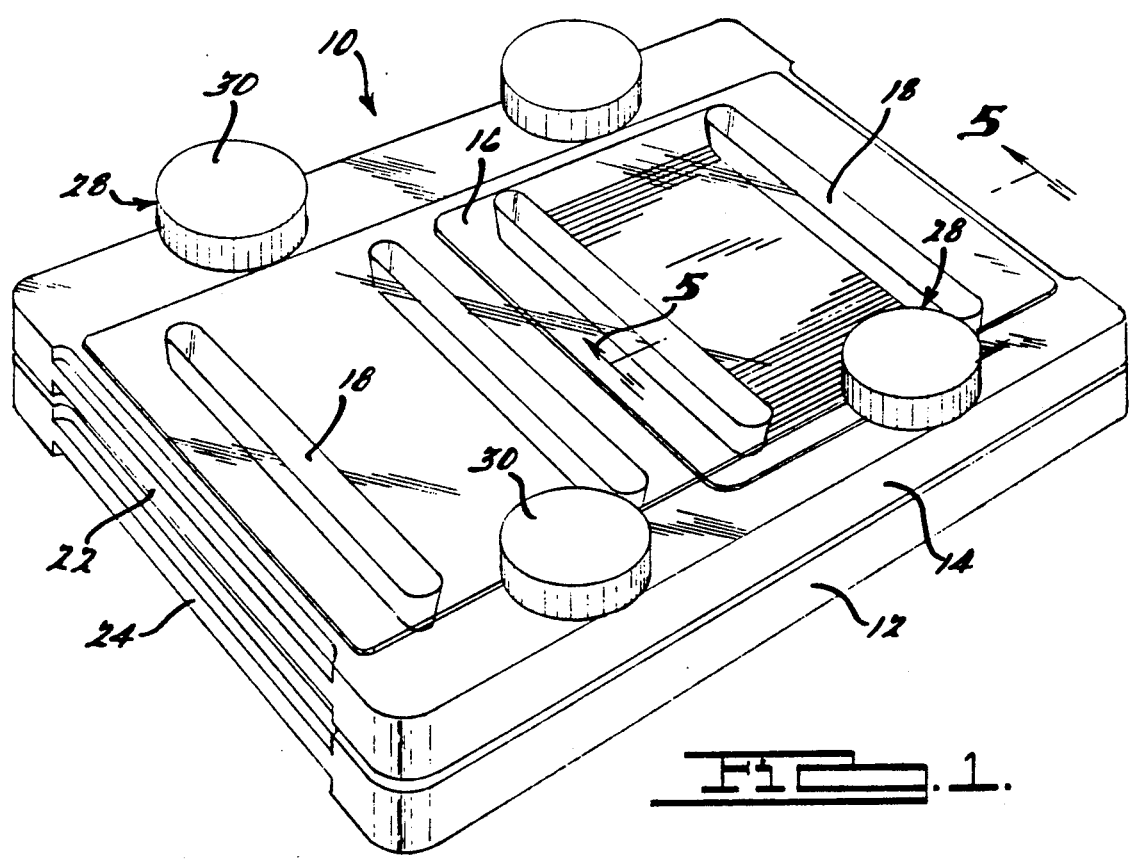
FIG. 1 is a perspective view of a first preferred embodiment of an assembled assay device of the present invention.

Referring first to FIG. 1, a perspective view of a first preferred embodiment of the assay device of the invention is shown assembled and is indicated generally by the numeral 10. Assay device 10 generally comprises base plate 12, cover plate 14 positioned parallel and superior to base plate 12, and a cassette 16 for receiving assay samples disposed between the plates. As shown in FIG. 1, cover 14 and base 12 plates are generally rectangular in shape, although their size and shape can vary provided that cassette 16 is suitably accommodated.

Figure 2:
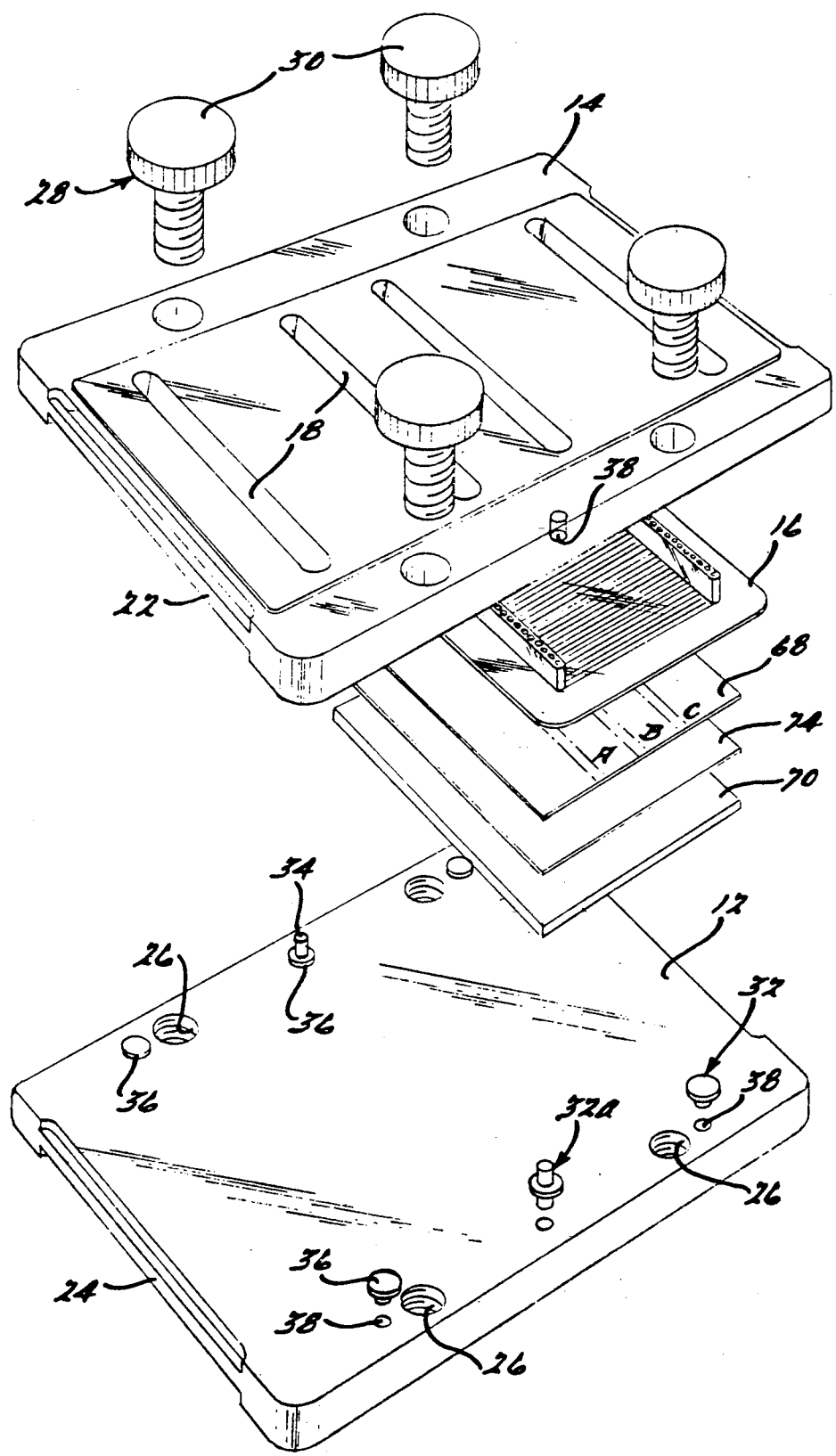
FIG. 2 is an exploded view of the assay device of FIG. 1.

Referring now to FIG. 1 and the exploded view of FIG. 2, cover plate 14 has a substantially planar body with two pairs of slots 18 extending therethrough. As described below in greater detail, each pair of slots 18 is adapted to receive a cassette 16. Thus, although only one cassette 16 is depicted in the Figures, it will be appreciated that two cassettes 16 can be accommodated by the embodiment shown. It will also be appreciated that the plates of the device of the invention can be designed for receipt of only one or virtually any number of cassettes.

As shown in FIG. 1 and later in the cross-sectional views of FIGS. 5 and 6, base plate 12 has a substantially planar body with supporting base feet 20 depending from its bottom surface. Both base and cover plates 12, 14 are also preferably recessed at opposing lateral edges to provide upper and lower handles 22, 24 which facilitate handling of the device and the individual plates. Base and cover plates 12, 14 are constructed of inert rigid materials which are resistant to the solutions and reagents used in the assay for which the device is intended. Shatter-resistant transparent plastic materials which permit visual observation of the assay are preferred, although materials such as glass, metal and opaque plastics such as ABS are also suitable. Preferred materials include poly(methyl methacrylate)-type polymers such as Plexiglas TM, polycarbonate resins such as Lexan TM, and polymethylpentene.

Referring now to FIG. 2, base and cover plates 12, 14 contain a plurality of corresponding screw holes 26, with base plate screw holes preferably being threaded, through which plate screws 28 are passed to fasten the plates together. It will, however, be appreciated that other means for fastening or clamping the plates of the device together can be utilized. As shown in FIGS. 1 and 2, screw heads 30 are large enough to permit easy manipulation by hand. Screw heads 30 are also preferably knurled, ridged, or otherwise textured to provide a good gripping surface. Screws 30 can be solid or hollow, but are constructed of inert rigid materials which are resistant to the solutions and reagents used in the assay. Suitable materials include both metal and plastics, preferably acetal plastics such as Delrin TM, nylon, ABS and Teflon TM.

Referring again to FIG. 2, assay device 10 is optionally provided with a series of spacers 32 disposed between base 12 and cover 14 plates. As shown in FIG. 2, a spacer shaft 34 extends from the head 36 of each spacer 32 and is received in a spacer hole 38 formed in the surface of base or cover plate 12, 14. Intermediately located spacers 32a have a dual arrangement of spacer shafts 34, which extend into spacer holes 38 in both base and cover plates 12, 14. This arrangement of spacers 32 serves to minimize lateral motion of the plates relative to one another. Spacers 32 can also, if desired, be employed to maintain a uniform interplate distance and a fixed degree of compression of cassette 16 between the plates of an assembled device. The interplate distance and degree of compression can, of course, be varied by changing spacer head dimensions and/or the resiliency of materials from which the spacers are constructed. It will be appreciated that spacer heads 36 can also be embedded or recessed, either partially or totally, in the plate surfaces to decrease or eliminate interplate distance. It will further be appreciated that spacers 32 may be eliminated from the device if so desired. Materials used in the construction of spacers 32 should be inert and resistant to assay solutions and reagents, and suitable materials include plastics, synthetic rubber and also metal.

Figure 3:
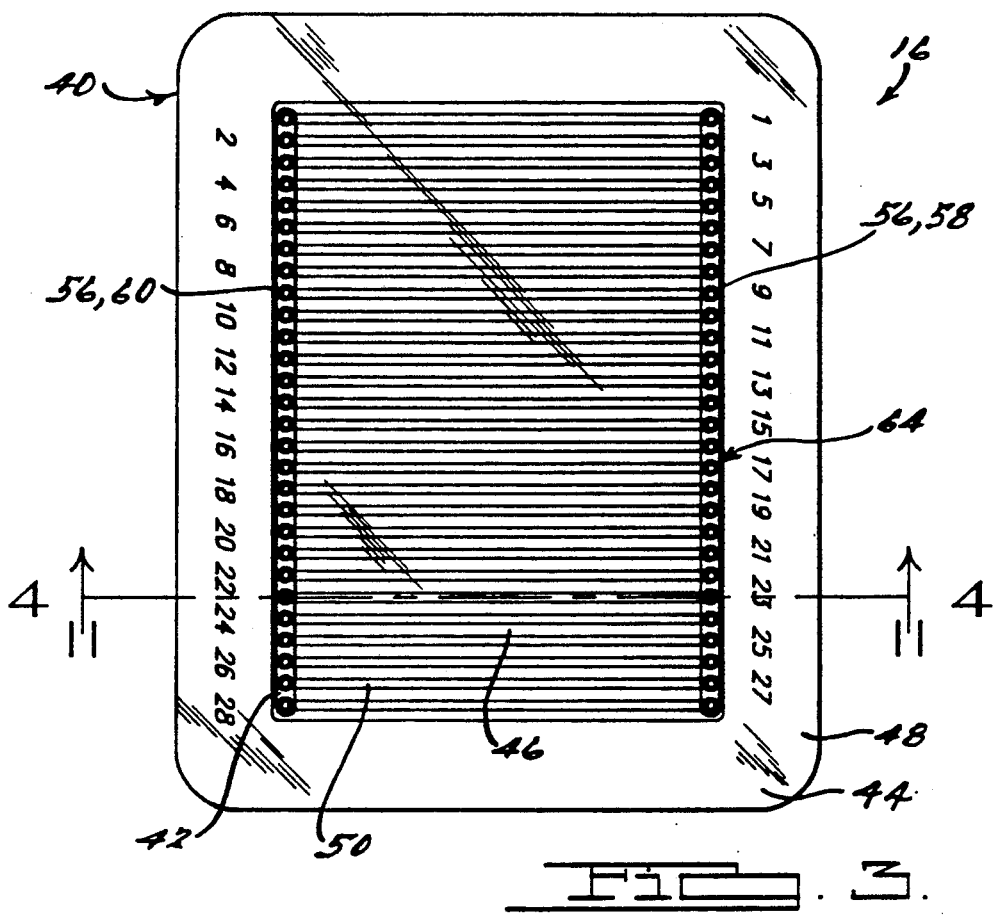
FIG. 3 is a top plan view of the cassette of FIGS. 1 and 2.
Figure 4A:
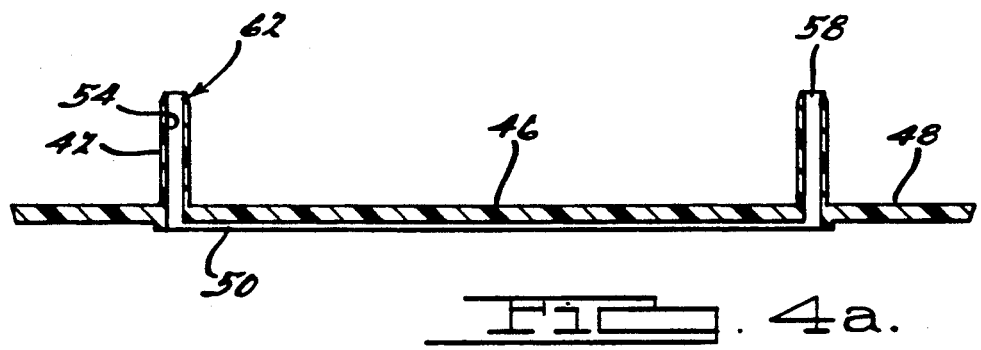
FIG. 4a is a cross-sectional view of the cassette taken along line 4—4 of FIG. 3.

Referring now to the top plan and cross-sectional views of FIGS. 3 and 4a, cassette 16 generally comprises a substantially planar cassette base 40 and a pair of opposing channel extensions 42 projecting perpendicularly from the top surface 44 of base 40. Cassette base 40 further comprises a channel portion 46 skirted by a flange portion 48. As shown in FIGS. 3 and 4a, channel portion 46 contains an array of parallel downwardly opening base channels 50 formed in base bottom surface 52. Channel extensions 42 also contain an array of parallel closed channels 54 corresponding to and in fluid communication with the open base channels 50. Although twenty-eight cassette channels are depicted in the Figures, it will be appreciated that the cassettes of the invention can contain any suitable number of channels. For conventional assays, five to thirty channels appear practical. The actual dimensions of the channels can also vary and may depend upon the assays for which the particular cassette is designed. However, the dimensions selected should be such that the results of the assay can be easily interpreted.

Figure 4B:
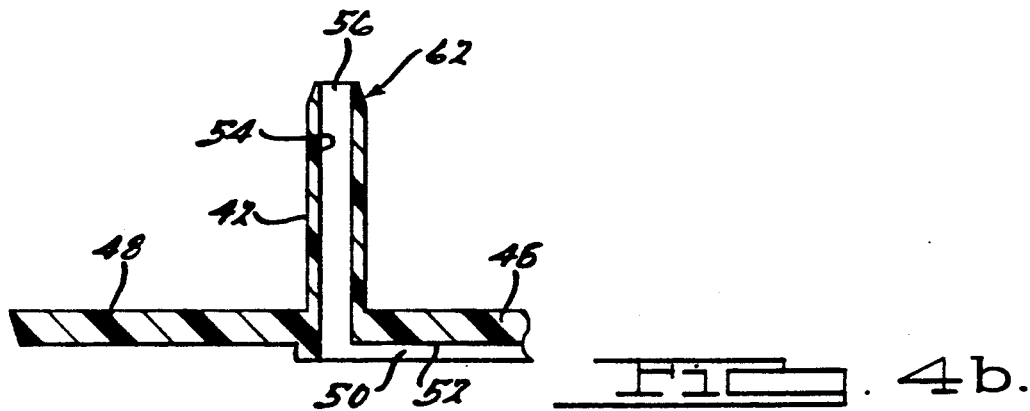

Referring to FIGS. 3, 4a and the enlarged view of FIG. 4b, each closed channel 54 of channel extension 42 terminates in a channel opening 56 which is designated channel inlet 58 or channel outlet 60 depending upon whether a fluid is being introduced into or removed from the channel through the opening. It will thus be appreciated that the channel openings can function as either inlets or outlets at the will of the user and that the designations in the Figures have been adopted merely for convenience.

Referring again to FIGS. 3 through 4a, channel extensions 42 of cassette 16 terminate in a cone-like channel lip 62 encircling each channel opening 56. Channel lip 62 assists in the introduction of samples, conventionally done by pipette, into closed channel 54 and reduces spillage and cross-contamination between channels. Preferably the tip of channel lip 62 is also colored as at 64 to contrast with channel extension 42 and act as an additional visual guide for the user.

As shown in FIG. 3, cassette base 40 preferably has numbers printed, engraved, stamped or otherwise affixed thereon to indicate the individual channels of the cassette 16. The numbering scheme can include every channel, every other channel or any other convenient system. Letters or other designations can also be employed.

Referring back to FIG. 2, when an assay is to be conducted, assay device 10 is provided with a membrane 68 on which a binding member specific for the analyte is immobilized. Typically the membrane comprises a flexible, nonwoven paper-like sheet of material such as nitrocellulose, nylon and combinations thereof, or other materials having similar immobilizing properties. In one preferred embodiment, proteins or nucleic acids are electrophoretically separated on a gel and transferred onto the membrane using Western, Northern or Southern blotting techniques well known to those skilled in the art. It should be appreciated, however, that a binding member can be immobilized on the membrane in any number of ways, including electrophoretically, chemically or physically.

In another preferred embodiment, a binding member is immobilized on the membrane without prior separation by charge or molecular weight or gel transfer to the membrane. Binding member in solution can instead be "painted" or otherwise physically applied onto the membrane. The binding member can thus be immobilized in a variety of configurations, including, for example, discrete spots, dots, bands or stripes. As shown schematically in FIG. 2, in one preferred embodiment several different binding members are immobilized on membrane 68 in bands A, B, and C which lie perpendicular to the cassette channels when membrane 68 is in place. Simultaneous screening for a variety of analytes can thus be accomplished on the same membrane for each assay sample introduced into a cassette channel. It will, however, be appreciated that a single or multiple bands of the same binding member can instead be immobilized on the membrane, and that different band orientations relative to the cassette channels may be utilized.

Referring again to FIG. 2, assay device 10 is further provided with a waterproof resilient pad 70. When assay device 10 is assembled as shown in the cross-sectional view of FIGS. 5 and 6, pad 70 is disposed between membrane 68 and the base plate 12. Pad 70 is preferably sized no smaller than membrane 68 and extends to flange portion 48 of cassette base 40, thereby covering the length of base channels 50. It should, however, be appreciated that pad 70 need only cover the channel in which the assay is being conducted if less than all channels are to be used. It should further be appreciated that either a single pad for the device or separate pads for each cassette 16 can be provided.

Figure 5:
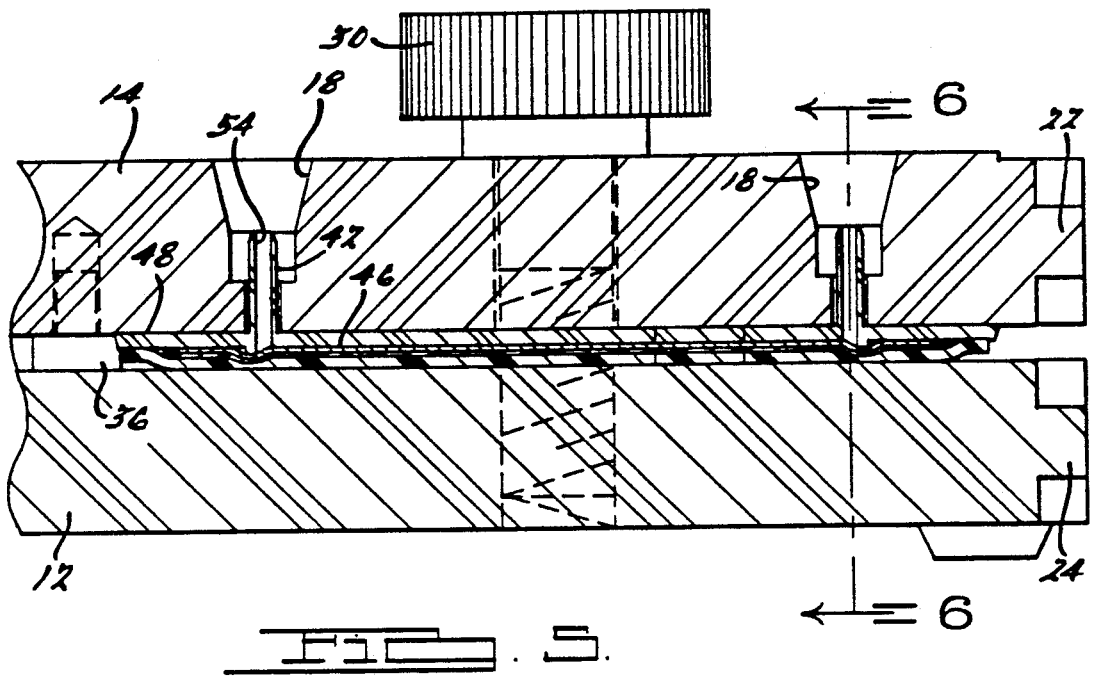
FIG. 5 is a cross-sectional view of the assembled assay device taken along line 5—5 of FIG. 1.
Figure 6:
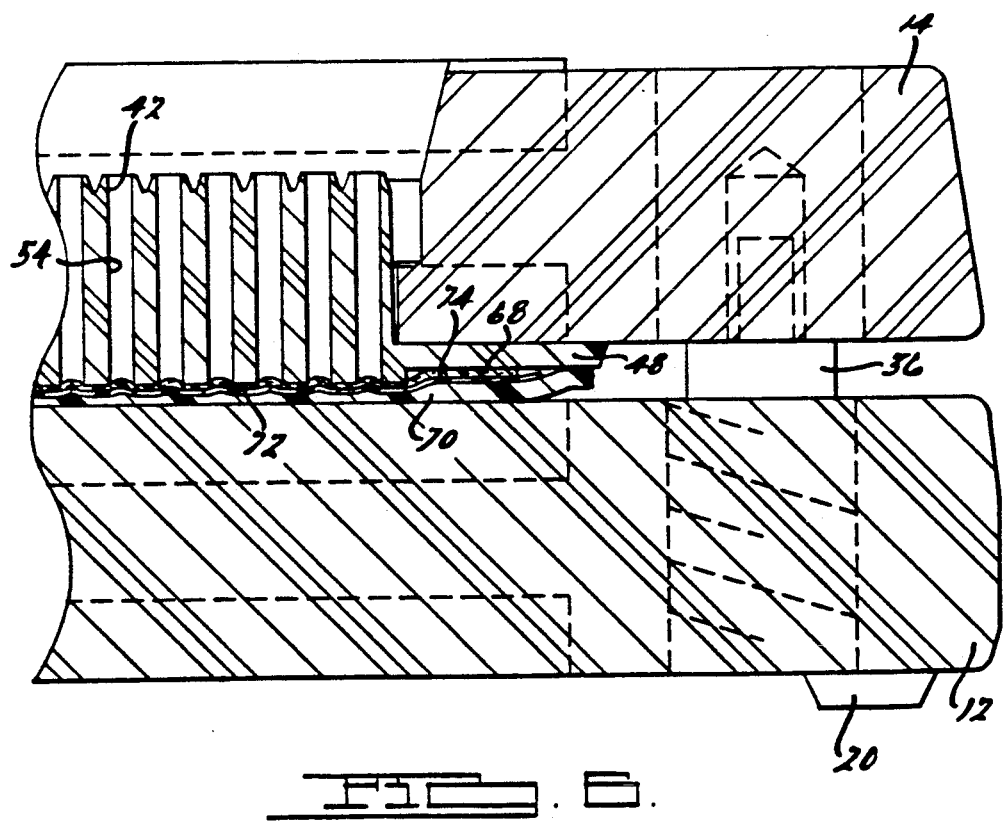
FIG. 6 is a cross-sectional view of the assembled assay device taken along line 6—6 of FIG. 5.

As shown in the cross-sectional views of FIGS. 5 and 6, when the plates of device 10 are secured together, the compression of pad 70 between base plate 12 and interchannel lands 72 produces a seal between base channels 50, thereby minimizing the risk of cross-channel migration and contamination of solutions between channels. As shown in FIG. 6, the compression of pad 70 also causes it to bulge into open base channels 50, thereby decreasing their volume and reducing the amount of test sample solutions required. When device 10 is assembled, pad 70 is preferably sealed by a peripheral adhesive layer (not shown) to flange portion 48 of cassette 16, although it will be appreciated that adhesive or other types of sealing are not necessary. Suitable materials for pad 70 include waterproof resilient materials such as rubber and open or closed cell plastic foams. For conventional assays, low density closed cell foams such as, e.g. polyethylene EZA copolymer Volara Type E sheets from Sekisui, a division of Voltech, having a density in the range of from about 2 lbs./ft.$^3$ to about 6 lbs./ft.$^3$ are examples of preferred materials. The thickness of pad 70 is preferably in the range of from about 1/64 in. to about ⅛ in.

Turning again to FIGS. 2, 5 and 6, cassette 16 is optionally provided with a gas-impermeable film 74 between membrane 68 and pad 70. Film 74 acts as a gas barrier to prevent gas diffusing into and forming bubbles in channels 50 during the assay. Film 74 is thus particularly advantageous when gas-releasing materials such as plastic foams are used for pad 70. Suitable materials for film 74 include plastic films such as polyurethane, polyethylene, and polyesters such as Mylar ™. Film 74 is preferably from about 1/1000 in. to about 1/100 in. in thickness, more preferably about 1/1000 in. thick.

Figure 7:
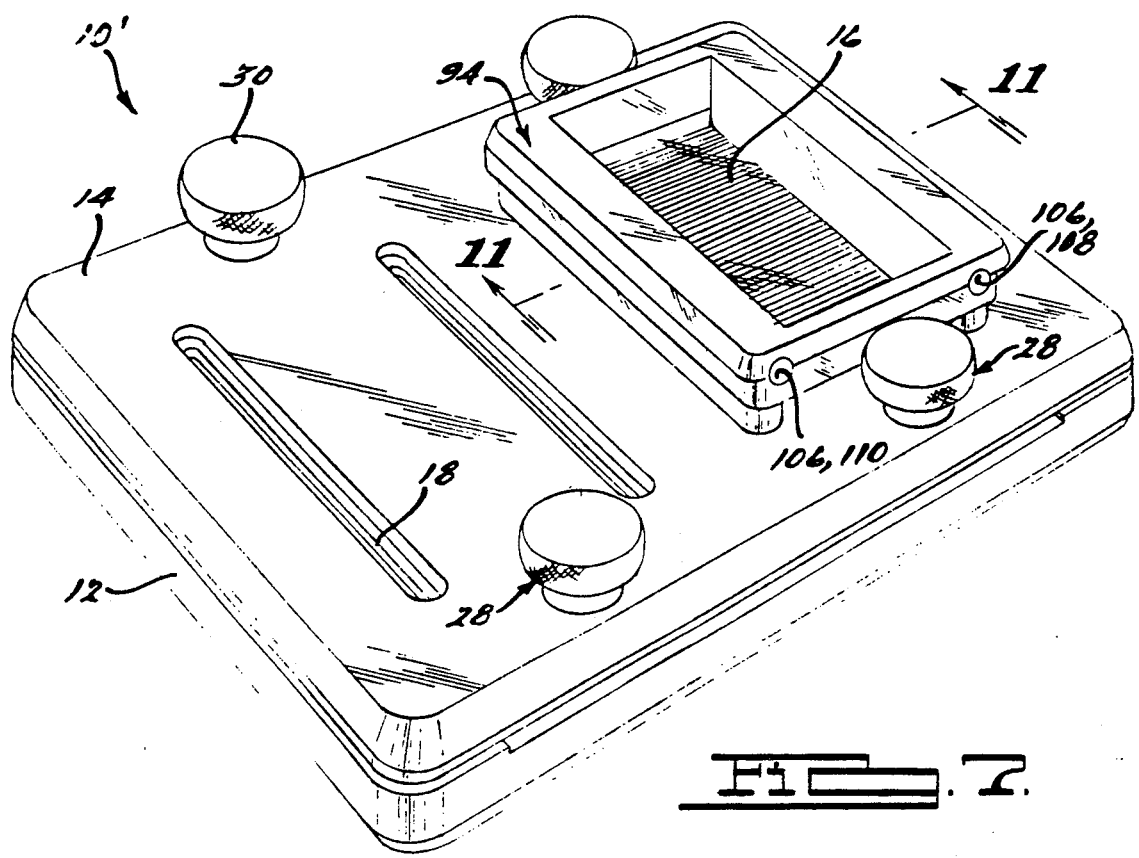
FIG. 7 is a perspective view of a second preferred embodiment of an assay device of the present invention.
Figure 8:
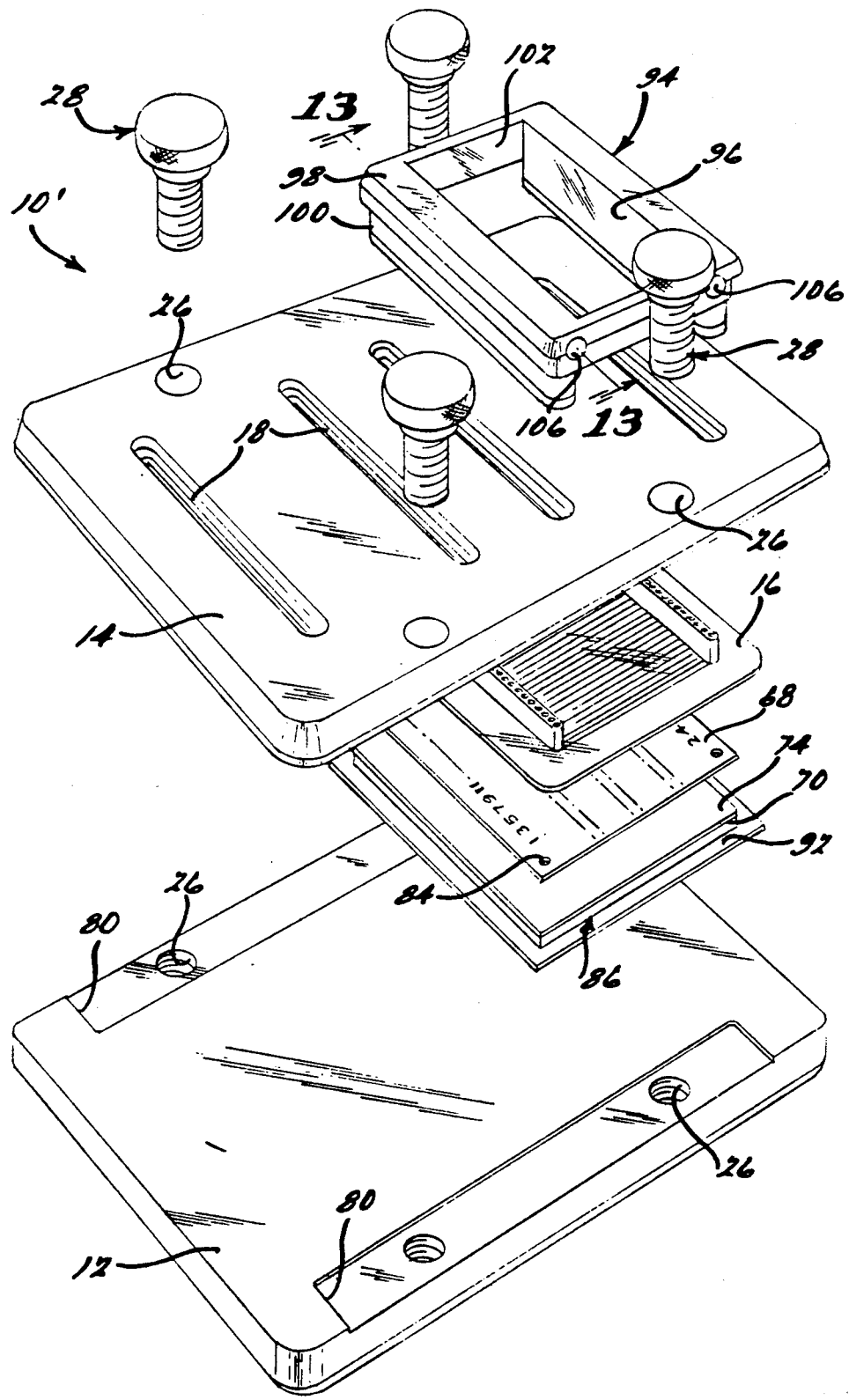
FIG. 8 is an exploded view of the assay device of FIG. 7.

Referring now to FIGS. 7 and 8, a second preferred embodiment of the assay device is shown and indicated generally by the numeral 10'. Features of assay device 10' common to assay device 10 have been described above and are denoted by the same numerals used in FIGS. 1 through 6. Additional or different features and modifications not described with respect to the first embodiment are discussed below.

Figure 9:
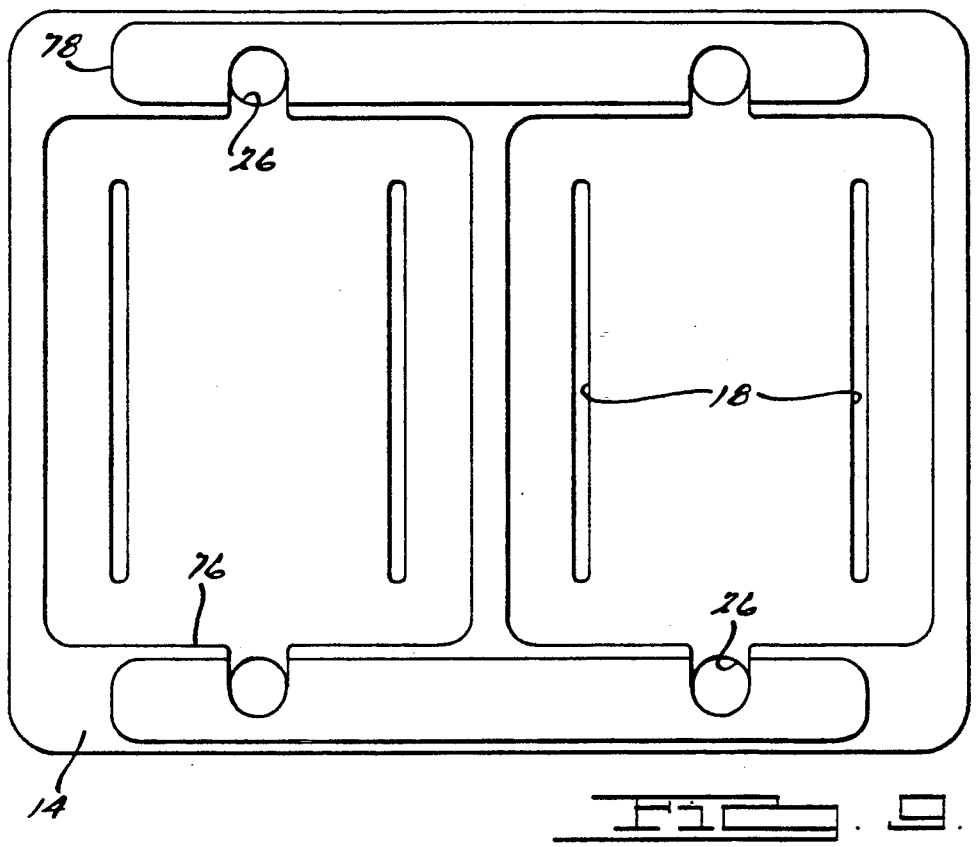
FIG. 9 is a bottom plan view of the cover plate of the assay device of FIGS. 7 and 8.

As shown in the bottom plan view of FIG. 9, the inner surface of cover plate 14 includes a cassette recess 76 which receives cassette base 40 when device 10' is assembled. Cover plate 14 further includes a pair of locking ridges 78 extending from its inner surface which nests into corresponding locking grooves 80 formed in the inner surface of base plate 12. This interlocking arrangement of the plates prevents gross lateral movement of the plates relative to one another and maintains an appropriate and uniform interplate distance, in turn providing uniform compression of the cassette 16 in an assembled device, if such compression is desired. The height of ridges 78 and depth of grooves 80 can be varied to increase or decrease or even eliminate the interplate distance.

Figure 10:
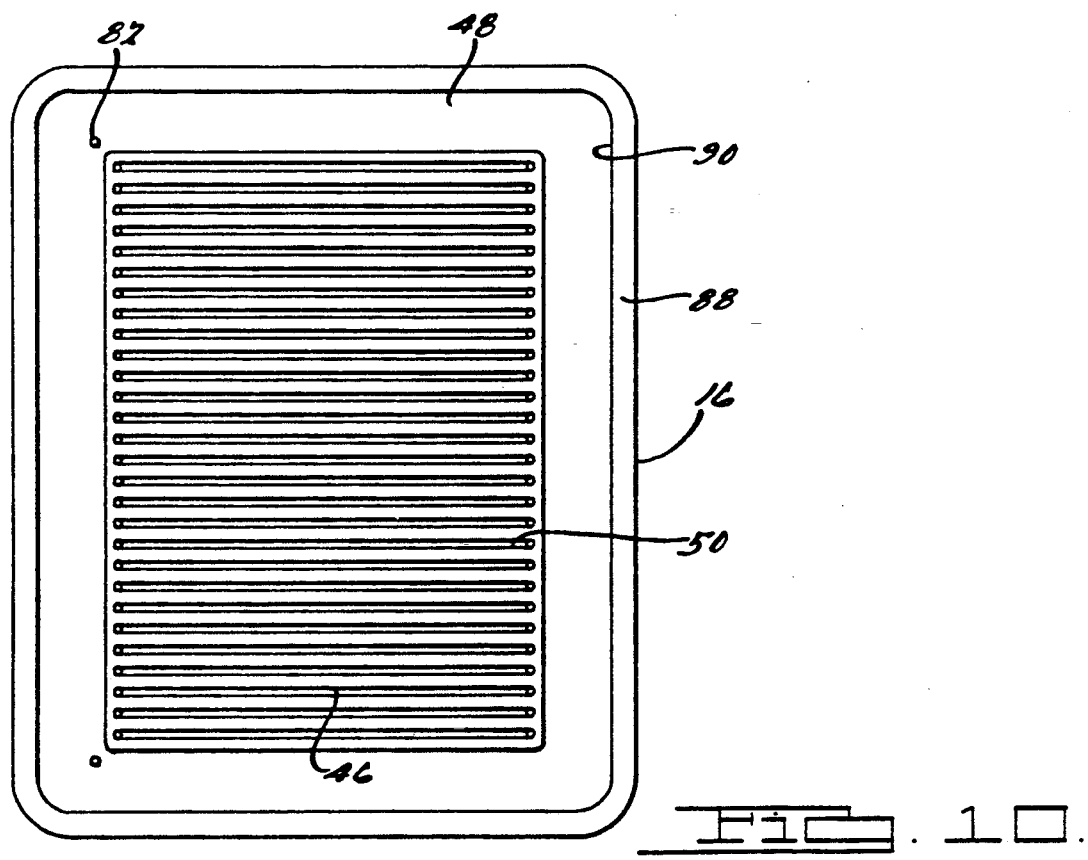
FIG. 10 is a bottom plan view of the cassette of the assay device of FIG. 8.

Referring now to the bottom plan view of FIG. 10, cassette base 40 further includes a pair of membrane pins 82 extending from its bottom surface 52 which engage a corresponding pair of membrane holes 84 at the corners of membrane 68. Membrane pins 82 thus help position membrane 68 on the cassette base 40 and prevent slippage of the membrane once it is in place. It should be appreciated that, although two membrane pins and holes are illustrated in the Figures, any suitable number can be employed.

Turning again to FIG. 8, in order to decrease the number of components handled, film 74 and pad 70 are preferably provided as a single laminated cushion 86. It will be appreciated, however, that the pad and film can also be provided separately as previously described.

Figure 11:
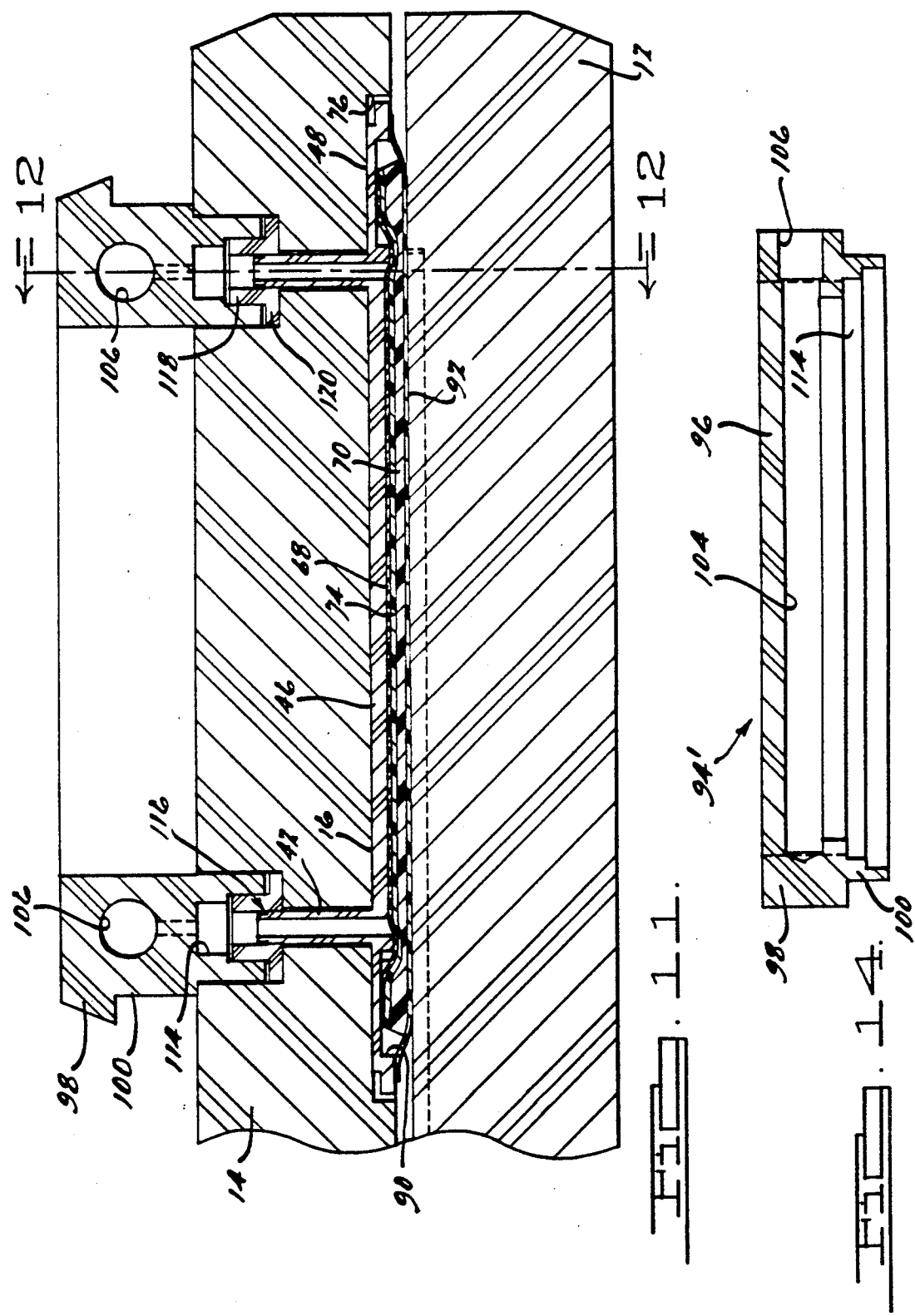
FIG. 11 is a cross-sectional view of the assembled assay device taken along line 11—11 of FIG. 7.
Figure 12:
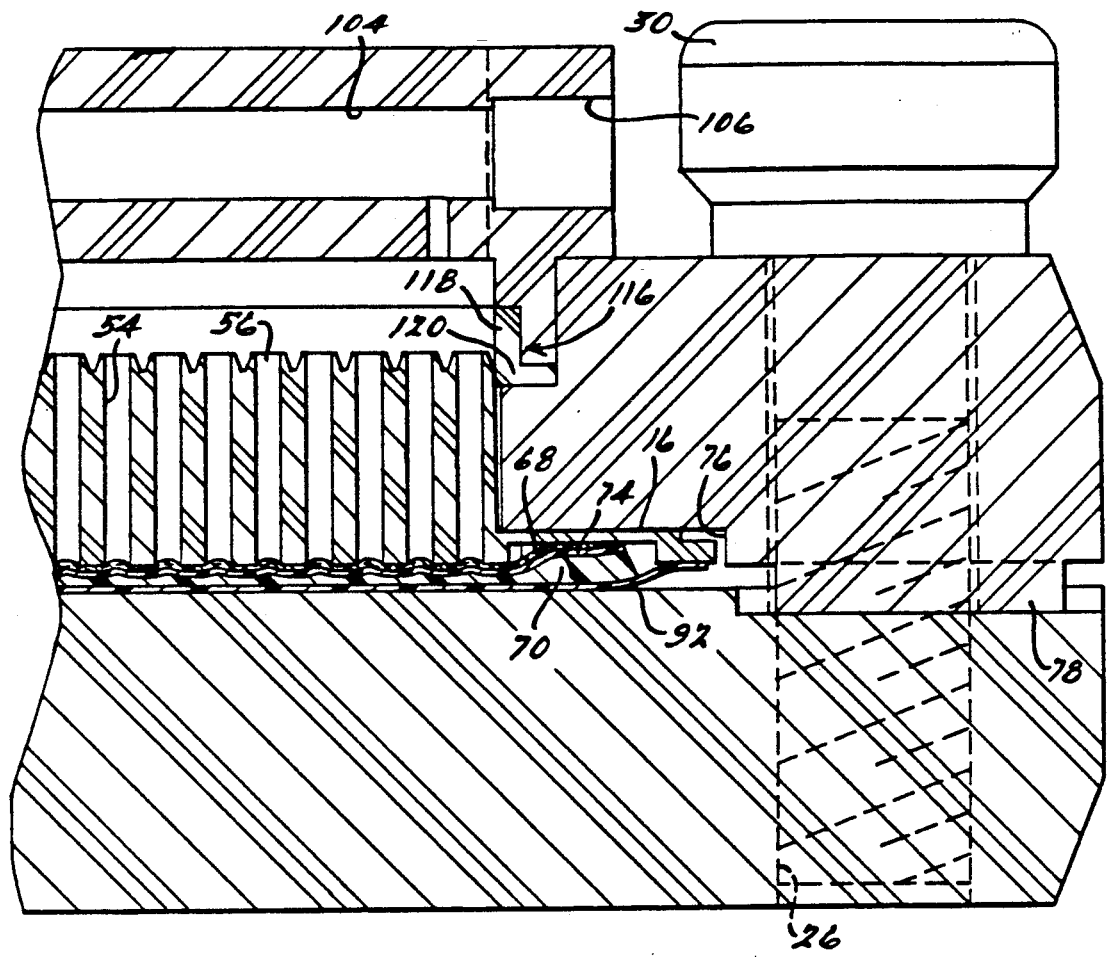
FIG. 12 is a cross-sectional view of the assembled assay device taken along line 12—12 of FIG. 11.

Referring now to FIGS. 10, 11 and 12, cassette base 40 terminates in a step-down peripheral rib 88, which together with channel portion 46 define a base recess 90 in bottom surface 52 of base 40. As discussed below, membrane 68 and cushion 86 can be packaged with cassette 16 in a waterproof plastic packaging sheet 92 sealed to the bottom surface of rib 88. Although packaging sheet 92 may be removed prior to the assay, it is contemplated that sheet 92 is left in place during the assay. Thus, when sheet 92 is sealed against rib 88, it will be appreciated that base recess 90 can also serve as a reservoir for solutions used during the assay. Suitable materials for packaging sheet 92 include polyester sheets or films such as Mylar TM which can be heat sealed to rib 88. It will also be appreciated that sheet 92 can be omitted, and cushion 86 or pad 70 and film 74 sized to extend to rib 88 which can serve as a point of adhesion or attachment to cassette 16.

Referring again to FIG. 8, membrane 68 can also include channel numbers, letters, or other designations embossed, imprinted or otherwise provided thereon to assist the user in proper channel determination. Preferably the numbering or other designations on membrane 68 will be on that portion of membrane 68 which extends into base recess 90 to reduce wear on the numbers or designations. It will be appreciated that this scheme can be used as an alternative or in conjunction with the numbering scheme previously described for the cassette.

As described above, it is contemplated that the cassette and membrane and, if desired, the resilient pad and film or cushion can be provided to the consumer as a preassembled unit. Such units can be supplied in sealed plastic packaging as described above or in separate moisture-proof packaging to avoid contamination and permit pre-moistening of the membrane, and to promote longevity of the package contents. It will be appreciated, however, that the components of the cassette unit of the invention can also be provided individually or together with the assay device plates. It will also be appreciated that, although the cassette, cushion, pad, and film can be cleaned and reused, the entire cassette unit or any of its components can be discarded after a single use.

Figure 13:
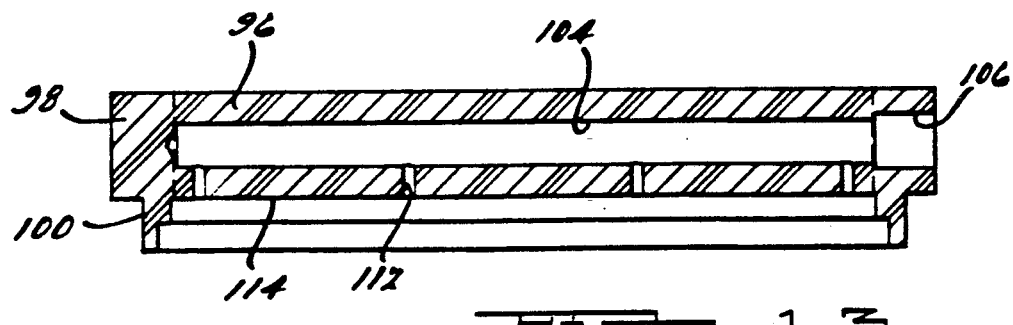
FIG. 13 is a cross-sectional view of the manifold cartridge taken along line 13—13 of FIG. 8.

Referring again to FIGS. 7 and 8, assay device 10' is provided with a removable twin manifold cartridge 94 for simultaneous filling or flushing of the channels of the device. Manifold cartridge 94 generally comprises a pair of elongated manifolds 96, each further comprising base 98 and leg 100 portions and connected by a manifold bridge 102. As better illustrated in the cross-sectional views of FIGS. 11 and 12, manifold base 98 contains a manifold channel 104 which extends substantially but not entirely through its length and terminates at one end in a manifold opening 106. As described above with respect to channel inlets 58 and outlets 60, designation of the manifold channels as inlet 108 or outlet 110 is dependent upon whether fluid is being introduced or removed from the manifold. As further shown in cross-section in FIGS. 12 and 13, a plurality of cross-channels 112 extend through manifold base 98 to connect manifold channel 104 with an elongated leg groove 114 formed in leg portion 100. It will be appreciated, however, that although four cross-channels are depicted in the Figures, any number or only one cross-channel can be employed in the practice of the invention.

When assay device 10' is assembled as shown in FIGS. 11 and 12, manifold leg portion 100 is inserted into cover plate slot 18. A resilient gasket 116 in sealing relationship with leg portion 100 and channel extension 42 is also preferably provided. Gasket 116 is generally L-shaped in cross-section, comprising side 118 and bottom 120 walls defining substantially a right angle. Side wall 118 is preferably affixed to the inner and bottom surfaces of leg portion 100 by an adhesive layer to secure gasket 116 in place during insertion of leg portion 100 into cover plate slot 18. Suitable materials for gasket 116 include chemically inert elastomeric materials and include materials such as, for example, natural and synthetic rubbers.

As shown in the assembled view of FIG. 11, channel extension 42 of cassette 16 extends into leg groove 114 of leg portion 100 residing in slot 18, thereby providing fluid communication between the channels of the cassette and those of the manifold. When simultaneous filling, flushing or washing of the channels of the cassette is desired, the fluid is introduced into manifold inlet 108. The fluid introduced into inlet 108 flows through channel 104, cross-channels 112 and leg groove 114 of the manifold, through cassette channel inlets 58 into closed channels 54, and continues onto base channels 50 which open onto membrane 68. From base channels 50, flow continues into the opposing manifold's leg groove 114, cross-channels 112 and channel 104, exiting through manifold outlet 110. Introduction into or removal of the fluid from the manifold may also be assisted by vacuum pump or pressure devices.

Turning now to FIG. 14, a cross-sectional view of another embodiment of manifold cartridge of the invention is shown and denoted by the numeral 94'. As shown in the Figure, the manifold channel and cross-channels are eliminated and the manifold opening 106 opens directly into leg groove 114, forming a single fluid chamber. This configuration of manifold cartridge allows for higher volume flushing in a shorter period of time, if such flushing is desired.

The manifold cartridge of the invention is constructed from suitably rigid and inert materials, preferably plastic materials such as those described for the construction of base and cover plates. Additionally, it will be appreciated that, although a twin manifold cartridge is depicted in the Figures, a single manifold or a pair of manifolds without any connecting bridge can also be employed in the practice of the present invention. It will also be appreciated that, although a removable manifold is shown in the preferred embodiment, a single or twin manifold of the invention can be molded integral with or affixed to the cover plate.

To conduct an assay with a device of the present invention such as device 10 or 10', membrane 68 with a binding member for the analyte of interest immobilized thereon is first provided. It will, of course, be appreciated that although the assay and device of the invention are discussed in terms of a single binding member and analyte, multiple binding members can be used to simultaneously screen for one or more analytes. If not preassembled, the cassette unit is assembled by positioning membrane 68 on the bottom surface 52 of cassette base 40 and placing film 74 and pad 70 or cushion 86 thereunder. The cassette unit is inserted between the cover 14 and base 12 plates, which are then screwed or otherwise fastened together to compress pad 70 or cushion 86 and form an interchannel seal between the cassette's base channels 50 which open onto membrane 68.

Once the device is assembled, test samples are introduced into the cassette under conditions which allow binding between binding member and analyte to occur. Samples are injected into channel inlets 58 and flow through closed channels 54 into the base channels 50 which open onto membrane 68. Other assay reagents or indicators may, of course, also be added. After sufficient opportunity has been given for binding events to have occurred on membrane 68, a manifold cartridge 94, 94' can be employed as previously described to rinse any unbound materials from the membrane. The device can then be disassembled and the membrane examined or further processed for evidence of binding events.

It is contemplated that the device of the present invention can be adapted for virtually any binding assay which can be conducted on a membrane, including direct or sandwich assays well known to those skilled in the art. In such assays analyte is bound to a binding member immobilized on the membrane, and a labelled second binding member is bound thereto to provide a detectable signal. It will also be appreciated that any variety of labels or indicator schemes which provide a detectable signal that analyte binding has occurred can be employed in the practice of the present invention. For example, direct labels such as fluorescent, radioactive and chromophoric labels can be used. Labels which may require development or enzymatic reagents, such as horseradish peroxidase or alkaline phosphatase, can also be utilized. It will likewise be appreciated that indirect label vehicles such as Protein A or avidin/biotin methods, know to those skilled in the art, can also be adapted for use with the device and assays of the present invention.

The assay device and binding assay of the invention are well-suited for conducting immunoassays for the presence of an antibody or antigen analyte in human serum, urine, stool, saliva or other body fluids, secretions or excretions. It will be appreciated, however, that the device and assays of the present invention can be adapted to utilize the binding affinity of any binding member such as, for example, haptens, complimentary nucleic acid sequences, ligand and receptors. The present invention can also be used to screen for the presence of microbial organisms, including bacteria, viruses and fungi. The device of the invention can additionally be used to screen or otherwise characterize binding specificities of monoclonal antibodies, antibodies of different species and antibodies produced by genetic engineering or other in vitro techniques.

Examples of binding assays which can be conducted with the device and in accordance with the principles of the present invention include assays for bacterial proteins of *Borrelia burgdorferi* which causes Lyme (erythema chronicum migrans) disease, for viral proteins of HSV which causes herpes, for viral proteins of HIV implicated in acquired immunodeficiency syndrome (AIDS), for human chorionic gonadotropin (HCG) to detect pregnancy, for rheumatoid arthritis, and for a variety of bacterial and viral infections. It is also contemplated that the device and assays of the present invention be used to screen for toxins such as, e.g. that of *Clostridium difficile*, and to screen for specific nucleic acid sequences to detect genetic defects.

The foregoing discussion discloses and describes merely exemplary embodiments of the present invention. One skilled in the art will readily recognize from such discussion, and from the accompanying drawings and claims, that various changes, modifications and variations can be made therein without department from the spirit and scope of the invention as defined in the following claims.

I claim:

1. An assay device for conducting a binding assay for an analyte of interest, the device generally comprising:
   a base plate having a substantially planar inner surface;
   a cover plate having a substantially planar inner surface positioned parallel and superior to base plate upper surface when the device is assembled, the cover plate further including a pair of parallel slots extending therethrough; and
   a removable cassette for receiving liquid samples disposed between the base and cover plate, the cassette generally comprising a substantially planar base portion having an array of downwardly opening base channels formed in its bottom surface, and further comprising a pair of channel extensions extending upwardly from the top surface of base portion and received by the slots of the cover plate when the device is assembled, each channel extension terminating in an array of channel openings leading into an array of parallel closed channels corresponding to and in fluid communication with the base channels.

2. The assay device of claim 1, further comprising a membrane placed in contact with one or more of the downwardly opening base channels, wherein the membrane has a binding member for the analyte of interest immobilized thereon.

3. The assay device of claim 1, further comprising fastening means for securing base and cover plates together.

4. The assay device of claim 3, wherein fastening means comprises a plurality of plate screws sized to snugly engage screw holes formed in base and cover plates.

5. The assay device of claim 3, further comprising a plurality of spacers positioned between the base and cover plates to maintain a uniform interplate distance.

6. The assay device of claim 1, wherein the inner surface of cover plate includes a recess sized to accommodate cassette base and which receives the cassette base when the device is assembled.

7. The assay device of claim 1, wherein at least one of the plates includes handles formed at opposing edges of the plate.

8. The assay device of claim 1, wherein the base plate includes a substantially planar outer surface opposing its inner surface and the base plate further comprises a plurality of base feet depending downwardly from its outer surface.

9. The assay device of claim 1, wherein the inner surface of one of the plates has a ridge extending from its inner surface and the inner surface of the opposing plate has a corresponding groove formed therein for nesting and interlocking receipt of the ridge to prevent gross lateral movement of the plates relative to one another when the device is assembled.

10. The assay device of claim 1, further comprising a manifold for the simultaneous introduction into or removal of liquids from the closed channels, the manifold generally comprising a base portion and a leg portion extending from base portion, the base portion having a manifold opening leading to a manifold channel formed therein and the leg portion having a leg groove in fluid communication with the manifold channel, wherein the leg groove is in fluid communication with the channel openings of the cassette.

11. The assay device of claim 10, wherein a channel extension of the cassette is nestingly received by the leg groove.

12. The assay device of claim 11, further comprising a gasket encircling the manifold leg portion in sealing engagement with a channel extension of the cassette.

13. The assay device of claim 10, wherein the manifold leg portion is integral with the cover plate.

14. An assay cassette for receiving multiple assay samples, the cassette generally comprising:
- a substantially planar base portion comprising a channel portion skirted by a flange portion, the channel portion containing an array of parallel downwardly opening base channels formed in its bottom surface; and
- a pair of channel extensions extending upwardly from the top surface of base portion, each channel extension containing an array of parallel closed channels corresponding to and in fluid communication with the base channels, wherein the closed channels terminate in channel openings for the introduction or removal of liquid assay samples.

15. The assay cassette of claim 14, further comprising a membrane having a binding member for an analyte of interest immobilized thereon placed against the bottom surface of the cassette in contact with the downwardly opening base channels of the cassette.

16. The assay cassette of claim 15, wherein more than one binding member is immobilized on the membrane.

17. The assay cassette of claim 16, wherein the binding members are for different analytes.

18. The assay cassette of claim 15, wherein the membrane includes channel designations visible thereon.

19. The assay cassette of claim 15, further comprising a waterproof resilient pad positioned below the membrane.

20. The assay cassette of claim 19, further comprising a gas impermeable film sandwiched between the membrane and the resilient pad.

21. The assay cassette of claim 20, wherein the gas impermeable film is laminated to the resilient pad.

22. The assay cassette of claim 20, further comprising a packaging sheet placed beneath the resilient pad and extending across a substantial portion of the bottom surface of the cassette.

23. The assay cassette of claim 15, further comprising a packaging sheet placed beneath the membrane and extending across a substantial portion of the bottom surface of cassette.

24. The assay cassette of claim 23, wherein the base portion further includes a peripheral rib extending from its bottom surface and the packaging sheet is sealed to the peripheral rib.

25. The assay cassette of claim 15, further comprising a plurality of membrane pins extending from the bottom surface of flange portion which engage a corresponding plurality of holes formed in membrane to secure membrane in position.

26. The assay cassette of claim 14, wherein each channel opening is defined by a cone-shaped tip.

27. The assay cassette of claim 26, wherein at least a portion of the tip is colored for optical contrast with the channel extension.

28. The assay cassette of claim 14, wherein the cassette includes channel designations visible thereon.

29. The assay cassette of claim 14, further comprising a first manifold for the introduction into or removal of liquids from the closed channels simultaneously, the manifold generally comprising a base portion and a leg portion extending from base portion, the base portion having a manifold opening leading to a manifold channel formed therein and the leg portion having a leg groove in fluid communication with the manifold channel, wherein a channel extension of the cassette is nestingly received by the leg groove placing leg groove in fluid communication with the channel openings of the cassette.

30. The assay cassette of claim 29, further comprising a second manifold substantially similar to and connected to the first manifold by a manifold bridge, wherein the leg groove of each manifold receives one of the pair of channel extensions of the cassette.

31. The assay cassette of claim 29, wherein the manifold channel and leg groove are connected by a cross-channel.

32. The assay cassette of claim 29, wherein the manifold channel and leg groove form a single fluid chamber.

33. An assay cassette unit for assaying multiple samples, the cassette unit generally comprising:
- a cassette comprising a substantially planar base portion, the base portion further comprising a channel portion skirted by a flange portion, wherein the channel portion contains an array of parallel downwardly opening base channels formed in its bottom surface, the cassette further comprising a pair of channel extensions extending upwardly from the top surface of base portion, each channel extension containing an array of parallel closed channels corresponding to and in fluid communication with the base channels, wherein the closed channels terminate in channel openings for the introduction or removal of liquid assay samples;
- a membrane having a binding member for an analyte of interest immobilized thereon placed against the bottom surface of the cassette in contact with the downwardly opening base channels of the cassette;
- a waterproof resilient pad positioned below the membrane;
- a gas impermeable film sandwiched between the membrane and the resilient pad; and
- a packaging sheet disposed beneath the resilient pad.

34. The assay cassette unit of claim 33, wherein the gas impermeable film is laminated to the pad.

35. The assay cassette unit of claim 33, wherein the packaging sheet is sealed to the bottom surface of the cassette.

36. The assay cassette unit of claim 33, wherein the unit is sealed from the environment.

37. The assay cassette unit of claim 36, wherein the membrane is premoistened.

* * * * *